(12) United States Patent
Atkin et al.

(10) Patent No.: US 6,579,258 B1
(45) Date of Patent: Jun. 17, 2003

(54) BREAST PUMP INSERT

(75) Inventors: Edward Atkin, London (GB); Roger Leonard Williams, Broxbourne (GB)

(73) Assignee: Cannon Rubber Limited, London (GB)

( * ) Notice: Subject to any disclaimer, the term of this patent is extended or adjusted under 35 U.S.C. 154(b) by 0 days.

(21) Appl. No.: 09/763,416

(22) PCT Filed: Aug. 23, 1999

(86) PCT No.: PCT/GB99/02780

§ 371 (c)(1),
(2), (4) Date: Apr. 19, 2001

(87) PCT Pub. No.: WO00/10625

PCT Pub. Date: Mar. 2, 2000

(30) Foreign Application Priority Data

Aug. 24, 1998 (GB) .............................................. 9818448

(51) Int. Cl.[7] ................................................ A61M 1/06
(52) U.S. Cl. ........................................... 604/74; 604/75
(58) Field of Search .............................. 604/74, 75, 76, 604/73, 35, 36, 132, 133, 346

(56) References Cited

U.S. PATENT DOCUMENTS

| | | | |
|---|---|---|---|
| 4,263,912 A | | 4/1981 | Adams |
| 4,799,922 A | * | 1/1989 | Beer et al. .................... 604/74 |
| 5,049,126 A | | 9/1991 | Larsson |
| 5,100,406 A | * | 3/1992 | Panchula .................... 604/74 |
| 5,885,246 A | * | 3/1999 | Ford ........................... 604/74 |

FOREIGN PATENT DOCUMENTS

| | | |
|---|---|---|
| FR | 1 067 421 | 6/1954 |
| GB | 2 297 913 | 8/1996 |
| WO | 98/22160 | 5/1998 |
| WO | 99/44650 | 9/1999 |

* cited by examiner

Primary Examiner—Manuel Mendez
(74) Attorney, Agent, or Firm—McDermott, Will & Emery

(57) ABSTRACT

A flexible resilient breast pump insert adapted to fit onto a vacuum generating breast pump operable to cyclically generate and release a negative pressure is disclosed. The insert has deformable zones (11, 14) spaced from each other along the longitudinal axis of the insert which are connected to the source of negative pressure so that the zones (11, 14) are deformed sequentially when the negative pressure is applied, to cause them to move inwardly and outwardly relative to the users nipple and areola and apply a peristaltic pressure thereto.

18 Claims, 3 Drawing Sheets

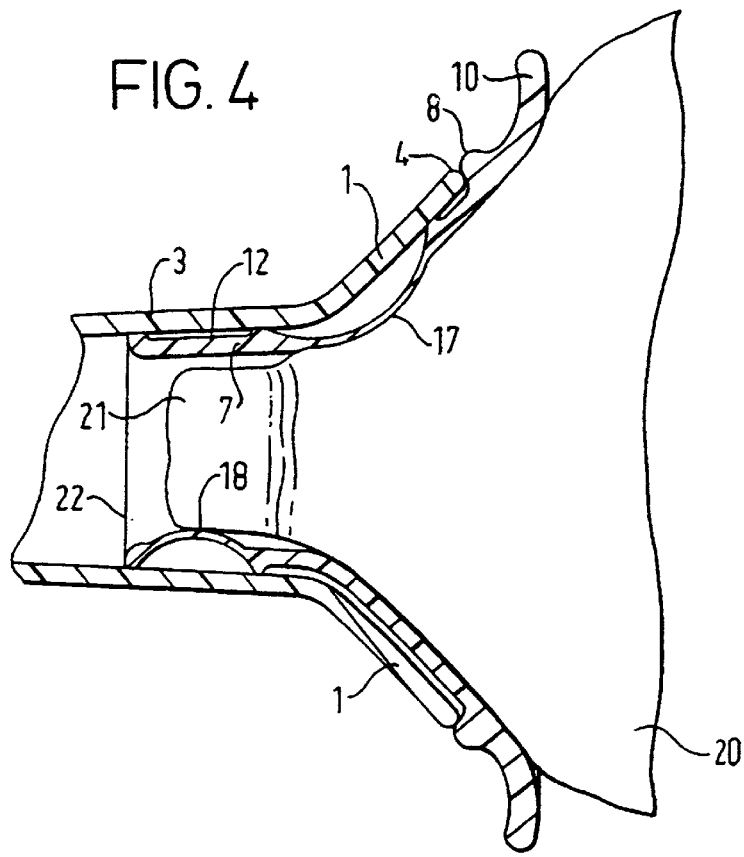
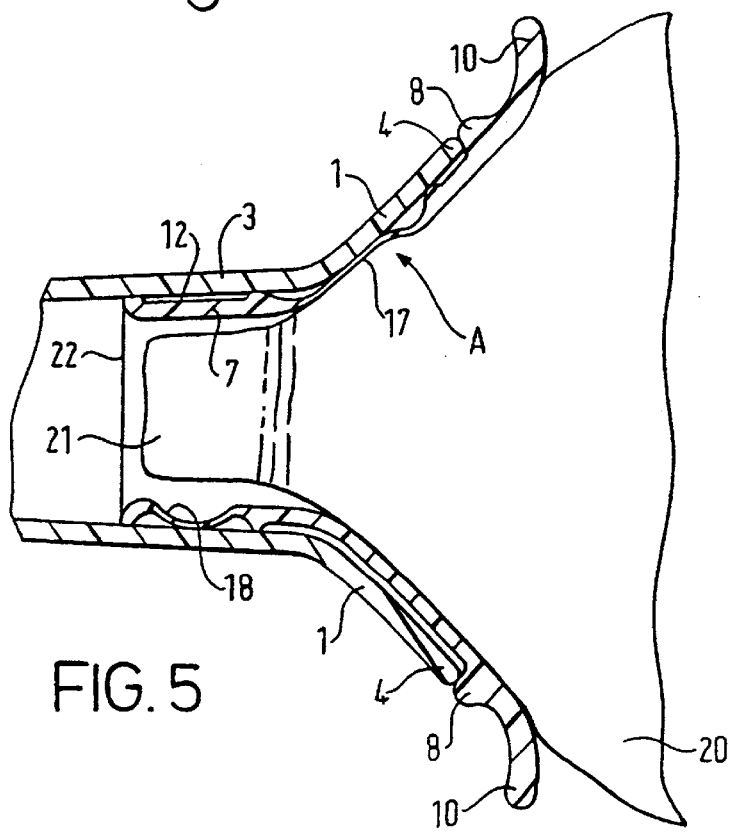

BREAST PUMP INSERT

This invention relates to a flexible resilient breast pump insert which is adapted to be fitted to a vacuum generating breast pump and more particularly to an insert which is designed to massage the user's nipple with a peristaltic action which resembles more closely the natural suckling action created by a baby.

Research has shown that when a baby is feeding at its mothers breast, it applies a peristaltic type of pressure to the mother's nipple sandwiched between its tongue and the roof of its mouth when it sucks on the nipple. This peristaltic pressure on the nipple draws milk from it. When the pressure is released, as the baby takes a breath, a new supply of milk flows into the nipple ready for the baby to extract it again once the "let down" reflex is activated due to the mothers "oxytocin" release.

It is known from GB 2297913A to provide a flexible resilient breast pump insert adapted to fit into a rigid funnel portion of a vacuum generating breast pump operable to generate a negative pressure, the insert comprising a mouth portion having an open end shaped to receive and contact the areola of a woman's breast and an inner portion of reduced size to receive the woman's nipple and having a wall with an inner and outer surface, connection means around the mouth portion to connect said mouth portion to a rigid breast pump funnel portion to form a pressure tight seal therewith, the mouth portion having a wall with an inner surface adapted to contact the woman's areola around the nipple and an outer surface with at least one recess formed therein, the thickness of the wall of the mouth portion in the region of the or each recess being less than that of the remainder of the mouth portion and means operable to connect the or each recess with the source of negative pressure. Whilst this insert has been found to work extremely well, it tends to apply pressure to the areola area of the breast rather than the nipple itself.

It is an object of the present invention therefore to provide an improved insert for use with a breast pump which is specifically designed to stimulate the area of the breast adjacent the nipple and the nipple itself when a cyclically generated negative pressure is applied to a mothers breast positioned within the insert.

A flexible resilient breast pump insert according to the present invention is characterised in that at least one additional recess is formed in the outer surface of the inner portion, the thickness of the wall of the inner portion in the region of the or each additional recess being less than the remainder of the inner portion; said means operable to connect the or each recess with the source of negative pressure also being operable to connect the or each additional recess with the source of negative pressure whereby, in use, the or each region of reduced wall thickness in the mouth and inner portion is deformed and deflected into contact with the inner surface of the rigid funnel portion of the breast pump in response to a negative pressure applied to the outer surface of the wall of said mouth and inner portion thereby massaging the areola and nipple region of the breast and stimulating the lactation of milk from the nipple.

In a preferred embodiment, the thickness of the wall of the mouth portion in the region of each recess is different to the thickness of the wall of the inner portion in the region of each additional recess, such that in use, the or each recess and the or each additional recess are sequentially deformed and deflected into contact with the inner surface of the rigid funnel portion of the breast pump in response to a negative pressure applied to the outer surface of the wall of said mouth portion, the recess and additional recess returning to their original configuration on release of the negative pressure.

Preferably, a plurality of inter connected discrete recesses spaced circumferentially around the insert are provided. Alternatively, there may be a single annular recess or pocket. Conveniently, the recesses are circumferentially spaced from each other by equal distance.

The connection means on the mouth portion can comprise an annular lip adapted to fit over and engage with the outer edge of the rigid funnel of the breast pump. Suitably the annular lip is molded to provide an undercut or rebate which cooperates with the connection means on the mouth portion to form a pressure tight seal therewith.

Conveniently, the means operable to connect the or each recess and the or each additional recess with the source of negative pressure is a pair of conduits or channels formed in the outer surface of the inner portion, one conduit leading from one of said recesses to the remote end of said inner portion of the insert, and the other conduit leading from one of said additional recesses to the remote end of the insert. The recesses can be any convenient shape but in the preferred embodiment, they are pear-shaped, the major axis of each recess being aligned with the main longitudinal axis of the insert, the additional recesses being generally circular. In this embodiment, the pear-shaped recesses are provided mainly on the mouth portion of the insert whereas the circular recesses are arranged circumferentially around the inner portion of the insert which receives the users nipple.

In the preferred embodiment, each conduit is an open channel formed in the outer surface of the wall of the inner portion and a continuous upstanding bead extends along both sides of the channels and around each recess and additional recess, said bead being operable, in use, to form a fluidtight seal with the inside surface of the funnel.

Preferably the or each recess and the or each additional recess protrudes inwardly from the inner surface of the insert. The bottom of each pocket is preferably arcuate to provide the or each protrusion. Due to the natural resilience of the material from which the insert is molded, each recess and each additional recess will deform outwardly into contact with the breast pump funnel on the application of a negative pressure thereto but it will reform to its normal configuration on release of the negative pressure due to the natural resilience of the material form which the insert is molded, preferably natural or synthetic rubber or silicon. It should be noted that it is an important feature of the invention that the gentle pressure is applied to the nipple or the areola as a result of the recesses and additional recesses reconfiguring to their original shape provides excellent stimulation for lactation. Thus, the negative pressure initially deforms the recesses and additional recesses in a direction away from the breast but they then reconfigure due to the natural resilience of the silicon rubber from which the insert is molded to apply a gentle pressure to the breast. In some of the prior art devices, the negative pressure deforms the recesses inwardly and draws them into firmer contact with the users breast thereby directly massaging it. Users have found these prior art arrangements to be unsatisfactory as too great a negative pressure can be applied directly to the breast and nipple area which the mothers find uncomfortable and it can make them tense which can result in poor lactation.

Preferably, the surface area of the or each recess is greater than that of the or each additional recess so that the or each recess of larger surface area will deform outwardly of the insert before the or each recess of lesser surface area for each cycle of negative pressured applied thereto. Alternatively, the thickness of the recess walls can be varied or a combination of both can be used.

The invention will now be described, by way of example only, with reference to the accompanying drawings, in which:

FIG. 4 is a schematic cross section of the flexible insert of FIGS. 1–3 showing a womans breast located therein; and FIG. 5 is a view similar to FIG. 4 but showing the insert in its deformed distorted condition with parts of the wall of the mouth portion contacting the inner surface of the rigid breast pump funnel.

Figure 2:
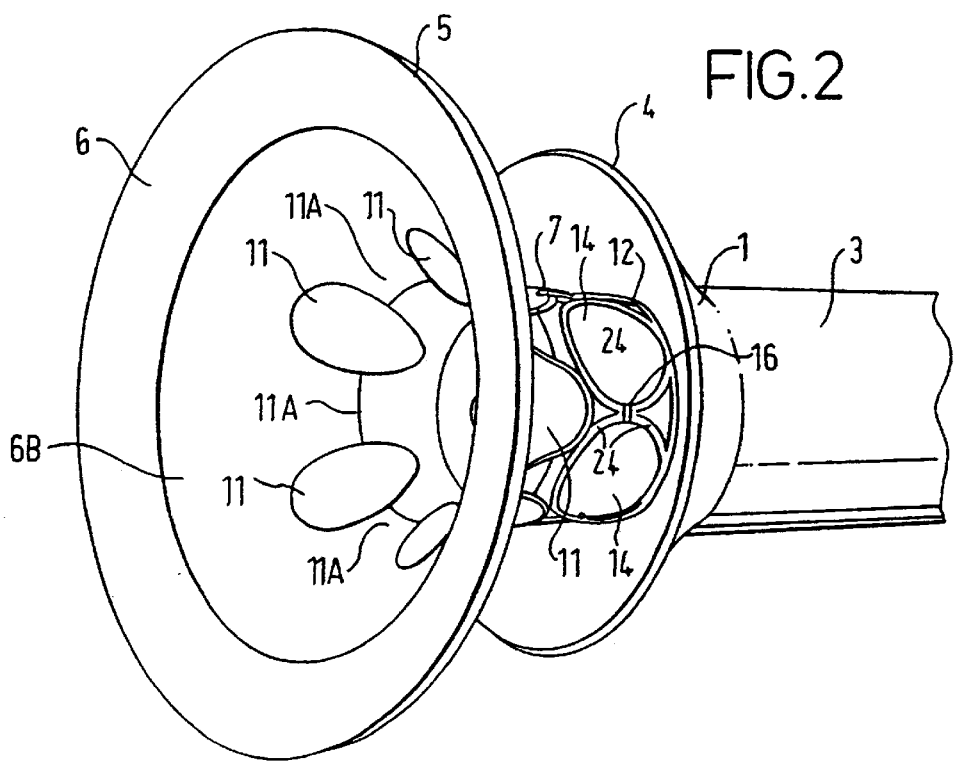
FIG. 2 is a perspective view of the flexible insert shown in FIG. 1, prior to insertion into the rigid funnel portion of a breast pump.

Referring to the drawings, there is shown in FIG. 2 a flexible resilient insert of the present invention just prior to insertion into the rigid funnel portion 1 of a known breast pump (not shown). The rigid funnel portion 1 is conical in shape and includes an inner tubular portion 3 extending forwardly therefrom and connected to the breast pump body (not shown). The rigid funnel portion 1 has a rim 4 around its periphery for reasons which will be explained hereafter.

The flexible insert 5 is molded in one-piece and includes a conical mouth portion 6 which is connected to a tubular inner portion 7 whose outer diameter is substantially equal to or slightly smaller than the internal diameter of the inner tubular portion 3 of the breast pump funnel. The mouth portion 6 is molded with an annular bead 8 which abuts rim 4 on the rigid funnel portion 1 of the breast pump to make a fluidtight seal therewith (see FIGS. 4 and 5). An annular flexible peripheral portion 10 extends circumferentially around the annular bead 8. The inner surface 6B of the mouth portion 6 is smooth as is the inner surface of the tubular inner portion 7.

Figure 1:
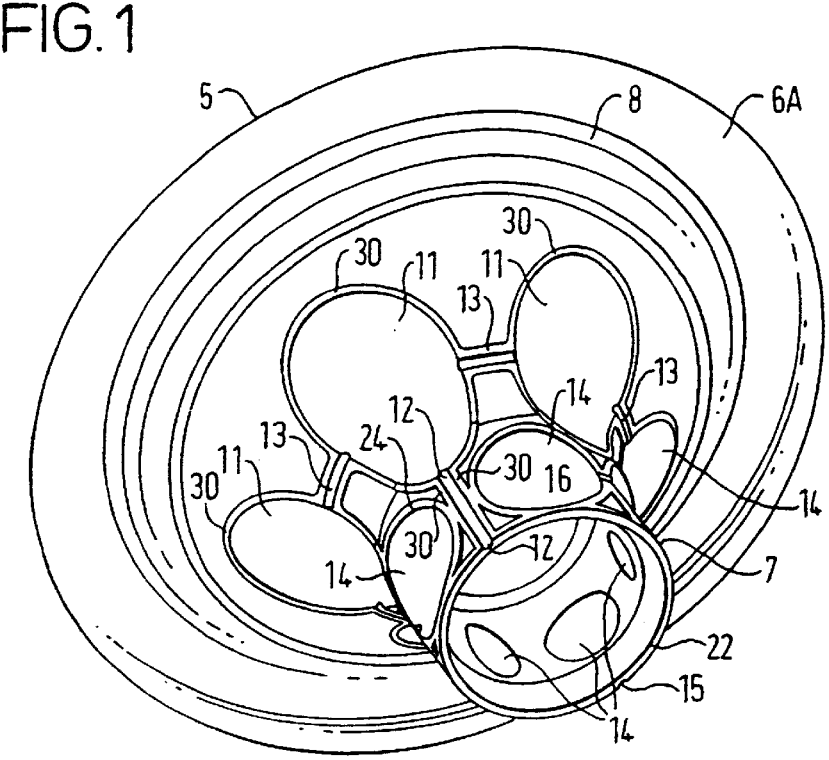
FIG. 1 is a perspective view showing a flexible insert of the present invention.

Referring now to FIG. 1, it can be seen that the outer surface 6A of the mouth portion 6 is formed with axially spaced deformable zones in the form of large and small deformable pockets 11 and 14. The first zone comprises the large pockets or recesses 11 on the mouth portion 6 whereas the second zone comprises the smaller circular pockets 14 around the tubular portion 7. The large pockets 11 are inter-connected by connecting conduits 13 and one of the large pockets 11 has a main conduit 12 extending therefrom to the inner periphery 22 of the tubular portion 7. Similarly, the smaller pockets 14 on the tubular portion 7 are interconnected by connecting conduits 16 and one of the smaller pockets 14 has a main conduit 15 extending therefrom to the inner peripheral edge 22 of the tubular portion 7 for reasons to be described hereafter. Thus, the large and small pockets 11 and 14 are connected to each other circumferentially but only one of the large or small pockets 11 or 14 is connectable to the source of negative pressure via the main conduits 12 and 15.

The main duct, conduit or channel 12 is molded into the outer surface of the inner tubular portion 7 and extends from the narrower end of the larger pockets 11 to end 22 of the inner tubular portion 7 for reasons to be explained hereafter. In the illustrated embodiment, there are five recesses or pockets 11 which are arranged circumferentially around the flexible mouth portion 6 and spaced apart by equal amounts to leave thicker fingers 11A therebetween (see FIG. 2). It will be appreciated that the thickness the mouth portion 6 in the region of the finger portions 11A is the full thickness of the mouth portion wall whereas in the pocket regions 11, the bottom wall of each pocket is of a reduced thickness. This can be seen better in the cross section views shown in FIGS. 3 and 4. Thus, the finger portions 11A provide harder portions around the mouth portion which in use, act on and stimulate the breast. Although five pockets 11 are illustrated, it will be appreciated that the number and configuration of the pockets is not critical. For instance, a continuous annular pocket could be formed in the mouth portion 6. As illustrated, an upstanding bead 30 extends between and alongside the main channel 12, around each pocket or recess 11 and alongside each connecting channel 13. In use, this bead 30 makes contact with the inner surface of the funnel (not shown) to form a fluidtight seal therewith. As a result, any leakage of vacuum from the recesses 11 is avoided or substantially reduced so that the users breast is more positively stimulated.

In the same way as has been described with reference to the larger pockets 11, a bead 24 also extends along each side of the main channel or duct 15 leading to the small pockets 14 and alongside each side of the ducts 16 connecting the small pockets 14 together and around the small pockets 14 themselves. This bead 24 makes a seal with the inner surface of the funnel (not shown) to form a fluidtight seal therewith and thereby prevent, in use, any leakage of vacuum from the small pockets 14.

Figure 3:
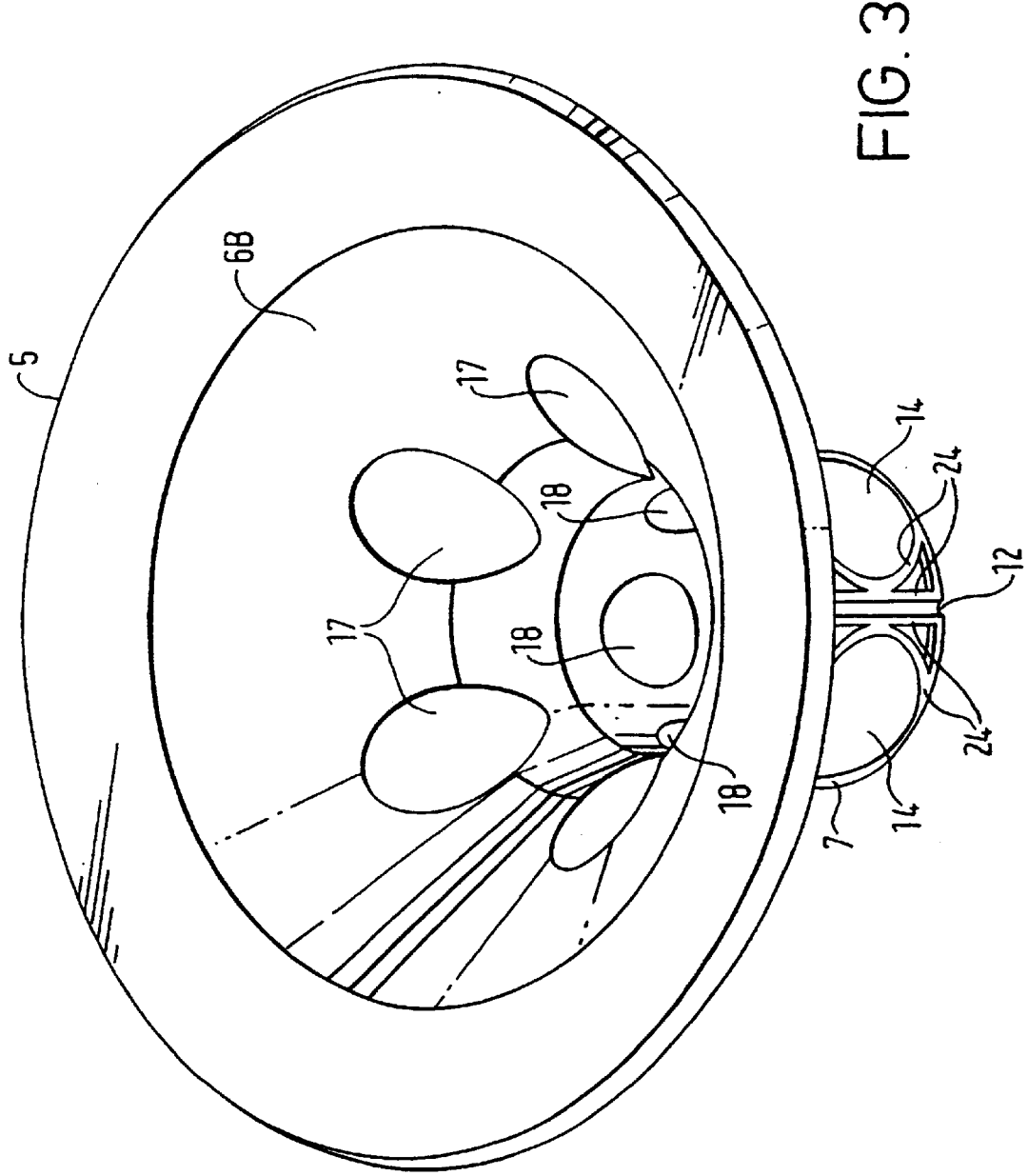
FIG. 3 is a top perspective view of the insert shown in FIGS. 1 and 2.

As can be seen from FIG. 3, each large recess 11 has an arcuate bottom wall 17 and each of the smaller pockets 14 has an arcuate bottom wall 18 both of which protrude beyond and inwardly of the frusto-conical main surface of the mouth portion 6 for reasons which will be explained hereafter.

In use, the flexible insert 5 is attached to the rigid breast pump funnel portion 1 by abutting the annular bead 8 against the rim 4 of the funnel to form an airtight seal therewith. The outer diameter of the inner tubular portion 7 of the flexible insert 5 is preferably slightly less than the inner diameter of the tubular portion 3 of the rigid funnel portion 1 of the breast pump although it can be of substantially the same diameter if necessary.

When the insert is properly attached to the rigid breast pump funnel portion 1, it assumes the position shown in FIGS. 4 and 5. FIG. 4 shows the position of the mothers breast 20 when inserted in the insert 5 and it can be seen that the breast fills the mouth portion 6. It will be noted however that only the areola is in contact with the inner surface of the conical mouth portion and thus with the protrusions 17. The nipple 21 protrudes into the tubular inner portion 7 our of contact with the inner walls thereof but contacted by the protrusions 18.

When a negative pressure is generated by the breast pump (not shown) in known manner, this causes the pockets 11, 14 to collapse sequentially and be sucked outwardly into contact with the inner surface of the conical portion 2 of the rigid funnel portion 1 of the breast pump as shown in FIG. 5, the space in the pockets communicating with the source of negative pressure by means of the main channels 12 and 15 and the inter connecting channels 13 and 16. Due to the pockets 11 being of a larger surface area than the pockets 14, they are deformed outwardly before the pockets 14. On release of the negative pressure, the pockets 11 and 14 return to their original configuration due to the natural resilience of the a material from which the insert is molded and thereby apply a gentle pressure to the areola 20 on the breast and nipple in a peristaltic way to encourage lactation. This process repeats on a cyclic basis to stimulate milk flow from the mothers breast when connected to the vacuum pump (not shown).

What is claimed is:

1. A flexible resilient breast pump insert adapted to fit into a rigid funnel portion of a vacuum generating breast pump operable to generate a negative pressure, the insert comprising a mouth portion having an open end shaped to receive and contact the areola of a woman's breast and an inner portion of reduced size to receive the woman's nipple and having a wall with an inner and outer surface, connection means around the mouth portion to connect said mouth portion to a rigid breast pump funnel portion to form a pressure tight seal therewith, the mouth portion having a wall with an inner surface adapted to contact the woman's areola around the nipple and an outer surface with at least one recess formed therein, the thickness of the wall of the mouth portion in the region of the or each recess being less than that of the remainder of the mouth portion and means operable to connect the or each recess with the source of negative pressure, characterised in that, at least one additional recess is formed in the outer surface of the inner portion, the thickness of the wall of the inner portion in the region of the or each additional recess being less than the remainder of the inner portion; said means operable to connect the or each recess with the source of negative pressure also being operable to connect the or each additional recess with the source of negative pressure whereby, in use, the or each region of reduced wall thickness in the mouth and inner portion is deformed and deflected into contact with the inner surface of the rigid funnel portion of the breast pump in response to a negative pressure applied to the outer surface of the wall of said mouth and inner portion thereby massaging the areola and nipple region of the breast and stimulating the lactation of milk from the nipple.

2. An insert as claimed in claim 1 wherein the thickness of the wall of the mouth portion in the region of each recess is different to the thickness of the wall of the inner portion in the region of each additional recess, such that in use, the or each recess and the or each additional recess are sequentially deformed and deflected into contact with the inner surface of the rigid funnel portion of the breast pump in response to a negative pressure applied to the outer surface of the wall of said mouth portion, the recess and additional recess returning to their original configuration on release of the negative pressure.

3. An insert as claimed in claim 1 wherein the or each recess and the or each additional recess are annular.

4. An insert as claimed in claim 1, including a plurality of inter-connected recesses spaced circumferentially around the insert.

5. An insert as claimed in claim 4, wherein the recesses are circumferentially spaced from each other by an equal distance.

6. An insert as claimed in claim 1, wherein the connection means on the mouth portion comprises an annular lip adapted to fit over and engage with the outer edge of the rigid funnel portion.

7. An insert as claimed in claim 6, wherein said annular lip is molded to provide an undercut or rebate.

8. An insert as claimed in claim 1, wherein the means operable to connect the or each recess and the or each additional recess with the source of negative pressure is a pair of conduit formed in the outer surface of the inner portion one conduit leading from one of said recesses to the remote end of said inner portion of the insert, and the other conduit leading from one of said additional recesses to the remote end of the insert.

9. An insert as claimed in claim 1 wherein the or each recess is pear-shaped, the major axis of each recess being aligned with the main longitudinal axis of the insert.

10. An insert as claimed in claim 1 wherein the additional recesses are generally circular and arranged circumferentially around the inner portion of the insert.

11. An insert as claimed in claim 8, wherein each conduit is an open channel formed in the wall of the inner portion.

12. An insert as claimed in claim 1 wherein a continuous upstanding bead extends along both sides of each channel and around the or each recess and the or each additional recess and is operable, in use, to form a fluidtight seal with the inner surface of the rigid funnel portion.

13. An insert as claimed in claim 1 wherein the or each recess and the or each additional recess protrudes inwardly from the inner surface of the insert.

14. An insert as claimed in claim 13 wherein the bottom of the or each recess and the or each additional recess is arcuate.

15. An insert as claimed in claim 13 wherein the bottom of the or each recess and the or each additional recess is planar.

16. An insert as claimed in claim 1 wherein the surface area of the or each recess is greater than that of the or each additional recess so that the or each recess of larger surface area will deform outwardly of the insert before the or each additional recess of lesser of surface area for each cycle of negative pressure applied thereto.

17. An insert as claimed in claim 1 wherein a third recess is provided on the insert.

18. An insert as claimed in claim 1 wherein molded from a natural synthetic rubber or silicone material.

* * * * *